United States Patent [19]

Kleiner

[11] 4,386,036
[45] May 31, 1983

[54] PROCESS FOR THE PREPARATION OF VINYLPHOSPHONIC ACID

[75] Inventor: Hans-Jerg Kleiner, Kronberg, Fed. Rep. of Germany

[73] Assignee: Hoechst Aktiengesellschaft, Frankfurt am Main, Fed. Rep. of Germany

[21] Appl. No.: 359,234

[22] Filed: Mar. 18, 1982

[30] Foreign Application Priority Data

Mar. 20, 1981 [DE]  Fed. Rep. of Germany ....... 3110975

[51] Int. Cl.³ ................................................ C07F 9/38
[52] U.S. Cl. ............................. 260/502.4 R; 260/983; 560/234
[58] Field of Search ................................. 260/502.4 R

[56] References Cited

U.S. PATENT DOCUMENTS 2,694,604 11/1954 Rogers et al. ................ 260/502.4 R
2,708,204  5/1955 Bell et al. ..................... 260/502.4 R
4,173,578 11/1979 Staendeke .................... 260/502.4 R

FOREIGN PATENT DOCUMENTS 2344332 3/1975 Fed. Rep. of Germany ... 260/502.4 R
 964330 7/1964 United Kingdom ......... 260/502.4 R

OTHER PUBLICATIONS

Canavan et al., "J. Chem. Soc.", Jan. 1962, pp. 331–334.

Primary Examiner—Joseph E. Evans
Attorney, Agent, or Firm—Curtis, Morris & Safford

[57] ABSTRACT

Process for the preparation of vinylphosphonic acid, by heating a 2-acetoxyethanephosphonic acid dialkyl ester of the general formula

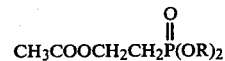

wherein R denotes an alkyl group having 1–4 carbon atoms, in the presence of acid or basic catalysts at 150° to 270° C. with elimination of an alkyl acetate, and thereafter hydrolyzing the remaining reaction mixture with water at temperatures between 150° and 230° C. while simultaneously distilling off the alcohol formed.

2 Claims, No Drawings

PROCESS FOR THE PREPARATION OF VINYLPHOSPHONIC ACID

It is known that pure vinylphosphonic acid can be obtained from vinylphosphoric acid dichloride. However, the synthesis of pure vinylphosphonic acid dichloride is technically elaborate. A simple process is therefore sought which produces technical grade crude vinylphosphonic acid.

It has now been found, surprisingly, that vinylphosphonic acid can be prepared in a simple and economical manner by heating a 2-acetoxyethanephosphonic acid dialkyl ester of the general formula

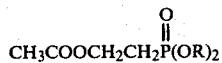

$$CH_3COOCH_2CH_2\overset{O}{\underset{\|}{P}}(OR)_2$$

wherein R denotes an alkyl group having 1 to 4, preferably 1 to 2, carbon atoms, in the presence of acid or basic catalysts at 150°–270° C., preferably 170°–230° C., alkyl acetates of the general formula

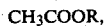

$$CH_3COOR,$$

wherein R has the abovementioned meaning, being eliminated, and thereafter hydrolyzing the remaining reaction mixture with water at temperatures between 130° and 230° C., preferably 140°–175° C., while simultaneously distilling off the alcohol formed of the general formula ROH, wherein R has the abovementioned meaning.

It is surprising that the mixture of various vinylphosphonic acid derivatives which is obtained on elimination of an alkyl acetate produces essentially vinylphosphonic acid on hydrolysis within the temperature range indicated.

Examples of possible starting materials are the dimethyl, diethyl, diisopropyl and di-n-butyl ester of 2-acetoxyethanephosphonic acid. The 2-acetoxyethanephosphonic acid dimethyl ester is particularly preferred.

Numerous compounds are possible as acid or basic catalysts. Acid catalysts used can be:

(A) sulfuric acid or phosphoric acid,
(B) halogen-containing carboxylic acids having a $P_{Ka}$ value <2.5, such as dichloroacetic acid, trichloroacetic acid or trifluoroacetic acid,
(C) aromatic sulfonic acids having a $P_{Ka}$ value <2.5, such as benzenesulfonic acid or p-toluenesulfonic acid,
(D) preferably phosphinic acids having 2 to 18 carbon atoms, such as dimethylphosphinic acid, methylethylphosphinic acid, dioctylphosphinic acid, methylphenylphosphinic acid or diphenylphosphinic acid,
(E) particularly preferably phosphonic acids having 1 to 18 carbon atoms and their half-esters having 1 to 4 carbon atoms in the alcohol radical, such as methanephosphonic acid, propanephosphonic acid, propanephosphonic acid monomethyl ester, octadecanephosphonic acid, 2-acetoxyethanephosphonic acid, 2-acetoxyethanephosphonic acid monomethyl ester, vinylphosphonic acid, vinylphosphonic acid monomethyl ester, vinylphosphonic acid monoethyl ester or benzenephosphonic acid,
(F) likewise particularly preferably pyrophosphonic acids or their half-esters, such as methanepyrophosphonic acid, benzenepyrophosphonic acid, vinylpyrophosphonic acid or vinylpyrophosphonic acid monomethyl ester,
(G) acid reaction mixtures which are produced in the process according to the invention are also highly suitable.

Basic catalysts used can be:

(A) Tertiary aliphatic and aromatic amines and phosphines having 3 to 18 carbon atoms, such as trimethylamine, tripropylamine, tributylamine, triphenylamine, trimethylphosphine, triethylphosphine, tripropylphosphine, tributylphosphine, triphenylphosphine and tris-(p-dimethylaminophenyl)-phosphine and the corresponding mixed amines, phosphines, phospholanes and phospholenes, such as dimethylethylamine, diethylbutylamine, N-dimethylaniline, 4-methyl-N-dimethylaniline, N-diethylaniline, N,N-tetramethylphenyldiamine or N-methylpyrrolidine; methyldiethylphosphine, dimethylpropylphosphine, diethylbenzylphosphine, 1-methylphosphol-3-ene and 1-ethyl-3-methylphosphol-3-ene.
(B) Quaternary ammonium salts and phosphonium salts having 3 to 18 carbon atoms, such as tetramethylammonium chloride, tetramethylammonium bromide or tetraethylphosphonium chloride, trimethylbenzylammonium chloride, triethylbenzylammonium chloride, triethylbenzylammonium bromide, trimethylbenzylphosphonium chloride or triphenylethylphosphonium-2,4-diaminobenzosulfonate.
(C) Heterocyclic compounds having aromatic character, such as pyridine, quinoline, their various alkyl and dialkyl, preferably methyl or dimethyl derivatives, imidazole, N-vinylimidazole, benzothiazole, 2-amino-6-ethoxybenzothiazole, and also phosphabenzoles;
(D) Acid amides, such as dimethylformamide, N-dimethylacetamide, N-diethylpropionamide, N-dimethylbenzamide, N-methylpyrrolidone or N,N'-tetramethylterephthalic acid diamide, or ureas, such as tetramethylurea or trimethylphenylurea.
(E) Other nitrogen compounds or phosphorus compounds having a valency of one N atom or P atom higher than 3, such as pyridine-N-oxide, trimethylphosphine oxide, tributylphosphine oxide, trihexylphosphine oxide, triphenylphosphine oxide, dimethylphenylphosphine oxide, dimethylphenylphosphine sulfide, dimethylchloromethylphosphine oxide, dimethyleicosylphosphine oxide, dimethyldodecylphosphine oxide, dimethylphosphine oxide, dimethylpyrrolidinyl-1-methylphosphine oxide, triphenylphosphine dichloride, dimethyldodecylphosphine sulfide, triphenylphosphineimine, dimethylchloromethylphosphine dichloride, N-2-dimethylphosphinylethylmethylacetamide or N-2-dimethylphosphinylethylmethylamine, or phospholene oxide, such as 1-methylphosphol-1-ene oxide or 1-ethyl-3-methylphosphol-1-ene oxide.
(F) Amides of phosphinous and phosphonous acid and of phosphinic and phosphonic acids and also their thio analogs, such as ethanephosphonic acid bis-diethylamide, methanebutanephosphinous acid dimethylamide or diethylphosphinous acid isobutylamide. Also triamides of phosphoric and of thiophosphoric acid, such as hexamethylphosphoric acid triamide.

The catalysts are used in amounts of 0.01 to 10, preferably 0.1 to 5, % by weight. When vinylphosphonic acid, monoalkyl esters thereof or acid reaction mixtures already obtained are used, even larger amounts of 10 to 50% by weight can be used.

The process is in general carried out by mixing the starting material with the catalyst and raising the mixture to the required reaction temperature of 150° to 270° C., preferably 170° to 230° C.

Higher temperatures are possible, but they do not yield any benefit. The danger of an increased formation of by-products, and also of polymerization, then arises.

The alkyl acetate being eliminated is then distilled off together with small amounts of an alkanol and of a dialkyl ether. The distillation is carried out under atmospheric pressure, if appropriate with the aid of an inert gas, such as, for example, nitrogen. However, in particular cases it may be advantageous to distil off in vacuo. The elimination of the alkyl acetate is complete after 2 to about 35 hours. It can be advantageous to continue stirring thereafter for another 1 to 4 hours at the reaction temperature, but also at higher temperatures. The process can also be carried out continuously.

It can be advantageous to add polymerization inhibitors, such as, for example, hydroquinone, hydroquinone monomethyl ether or phenothiazine.

If 2-acetoxyethanephosphonic acid diesters which are contaminated from their preparation with small amounts of the corresponding monoester are used as a starting material, a further addition of a catalyst is not necessarily required. It is here advantageous to start the reaction at about 250° C. When the acid reaction product which actually also acts as a catalyst for the elimination has been formed to a sufficient extent, the process can be continued at lower temperatures, for example at 180° to 220° C.

The reaction mixture produced in this elimination reaction essentially contains vinylphosphonic acid derivatives, vinylpyrophosphonic acid derivatives, oligomeric pyrophosphonic acid derivatives and derivatives of 2-hydroxyethanephosphonic acid together with phosphoric acid derivatives. The reaction mixture is then reacted, in the form in which it is obtained, at the required reaction temperature with water, the resulting alcohol being advantageously distilled off via a column. This reaction can produce small amounts of a dialkyl ether and of olefins. The reaction with water is complete when no more alcohol is eliminated. It can be advantageous in this reaction to employ larger amounts of water towards the end of the reaction and to distill off a part of the unreacted water together with the alcohol. The pressure to be selected according to the process is not critical, but the process is preferably carried out under approximately atmospheric pressure.

The reaction temperatures in this process step are between 130°–230° C. The reaction can also be carried out above 230° C., but a decomposition of vinylphosphonic acid must then be expected to take place to an increasing extent. The reaction is preferably carried out within the temperature range of 140° to 175° C. The reaction with water can also be carried out continuously. The resulting vinylphosphonic acid contains in addition to 2-hydroxyethanephosphonic acid or derivatives of 2-hydroxyethanephosphonic acid, in particular also phosphoric acid. The resulting vinylphosphonic acid is suitable for use as a corrosion inhibitor in aqueous systems. It is particularly suitable for use as an intermediate product in the preparation of flame-retardant agents. Interesting flame-retardant agents are obtained, if, for example, vinylphosphonic acid is reacted with vinylphosphonic acid dichloride and/or propanephosphonic acid dichloride and the resulting reaction material is further reacted with ethylene oxide. It is also possible to separate vinylphosphonic acid via its salts from the by-products, in particular from phosphoric acid.

EXAMPLE 1

100 g of 2-acetoxyethanephosphonic acid dimethyl ester were heated for 2 hours with stirring at 220°–230° C., while a mixture of 200 g of 2-acetoxyethanephosphonic acid dimethyl ester and 3 g of 4-(dimethylamino)-pyridine was added dropwise. Methyl acetate was simultaneously distilled off. The reaction batch was maintained for a further 3.5 hours at 210° C., and then finally for a further 30 minutes at 200°–210° C., during which period methyl acetae continued to be distilled off. A total of 112 g of methyl acetate was distilled off and 5 g of dimethyl ether were collected in a cold trap downstream of the apparatus. Water was metered in for 4 hours at 160° C. with stirring to the resulting mixture of vinylphosphonic acid derivatives, during which period methanol was distilled off via a column with a silver-coated jacket. When the methanol elimination was complete, the mixture was cooled to 90° C., and water still present in the dissolved state in the reaction batch was distilled off at this temperature under 0.5 mm Hg. 164 g of a reaction product were finally obtained, which contained 77% of vinylphosphonic acid, 5.1% of vinylphosphonic acid ester of 2-hydroxyethanephosphonic acid of the structure

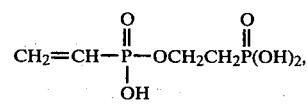

4.1% of 2-hydroxyethanephosphonic acid and 8% of phosphoric acid, relative to the total amount of phosphorus signals in a $^{31}$P-NMR spectrum.

EXAMPLE 2

100 g of 2-acetoxyethanephosphonic acid dimethyl ester were heated for 2 hours with stirring at 230° C., while a mixture of 200 g of 2-acetoxyethanephosphonic acid dimethyl ester and 30 g of vinylphosphonic acid was added dropwise. Methyl acetate was simultaneously distilled off. Stirring was continued for 1 hour at 200° C. Water was metered in in the course of 2.5 hours with stirring at 160° C. to the resulting mixture of vinylphosphonic acid derivatives, during which period methanol was distilled off via a column with a silver-coated jacket. 202 g of a reaction product were obtained, which contained about 4% of water. The reaction product also contained 76% of vinylphosphonic acid, 5% of vinylphosphonic acid ester of 2-hydroxyethanephosphonic acid of the structure

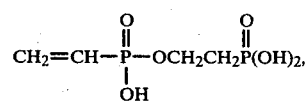

3.2% of 2-hydroxyethanephosphonic acid and 9% of phosphoric acid, relative to the total amount of phosphorus signals in a $^{31}$P-NMR spectrum.

EXAMPLE 3

80 g of 2-acetoxyethanephosphonic acid diethyl ester and 30 g of vinylphosphonic acid were mixed and the mixture was heated with stirring to 180° C. 400 g of 2-acetoxyethanephosphonic acid diethyl ester were then gradually added dropwise at first for 5 hours at 175°–180° C., and then for 19 hours at 185°–190° C. The mixture was then maintained at 200° C. for 1 hour. Ethyl acetate was distilled off during the entire reaction period and totalled 190 g. 2 g were collected in a cold trap downstream of the apparatus. 192 g of a vinylphosphonic acid derivative mixture were obtained. 149 g of this mixture were heated with stirring at 160° C. and water was gradually added dropwise for 5 hours, during which period ethanol was distilled off via a column with a silver-coated jacket. 143 g of a reaction product were obtained which contained 72% of vinylphosphonic acid, 7.3% of vinylphosphonic acid ester of 2-hydroxyethanephosphonic acid of the structure

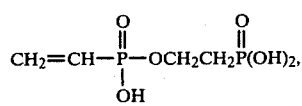

5.5% of 2-hydroxyethanephosphonic acid and 7.3% of phosphoric acid, relative to the total amount of phosphorus signals in a $^{31}$P-NMR spectrum.

EXAMPLE 4

200 g of 2-acetoxyethanephosphonic acid dimethyl ester and 10 g of triphenylphosphine were heated with stirring at 210°–225° C. 71 g of methyl acetate (94% of theory) were distilled off in the course of 3.5 hours. Stirring was continued for one hour at the reaction temperature. 124 g of a reaction product remained, which was reacted with water at 170° C. in a manner corresponding to Example 1. 112 g of crude vinylphosphonic acid were obtained.

EXAMPLE 5

300 g of 2-acetoxyethanephosphonic acid dimethyl ester, which contained 1 g of 2-acetoxyethanephosphonic acid monomethyl ester owing to its manner of preparation, were heated for 1 hour with stirring at 246° C. and then for 3 hours at 220° to 230° C. 108 g of methyl acetate which contained 2.4% of methanol and 2.5% of dimethyl ether, were distilled off via a column. 6.5 g of methyl acetate and 3 g of dimethyl ether were collected in a cold trap downstream of the apparatus. Stirring was continued for 1 hour at 210° to 230° C. Another 6 g of low-boiling products were collected in the cold trap downstream of the apparatus. 170 g of a reaction product remained, which were reacted with water at 160° C. in a manner corresponding to Example 1. 165 g of crude vinylphosphonic acid were obtained.

EXAMPLE 6

300 g of 2-acetoxyethanephosphonic acid dimethyl ester and 6 g of phosphoric acid tris-dimethylamide were heated with stirring for 7 hours at 200° to 220° C. 105 g of methyl acetate were distilled off via a column during this period. 8 g of low-boiling products were collected in a cold trap downstream of the apparatus. 182 g of a reaction mixture were obtained, which were reacted with water at 165° C. in a manner corresponding to Example 1. 163 g of crude vinylphosphonic acid were obtained.

EXAMPLE 7

300 g of 2-acetoxyethanephosphonic acid dimethyl ester and 3 g of trimethylphosphine oxide were heated with stirring for 8.5 hours at 200° to 220° C. 93 g of methyl acetate were distilled off during this period. 7.5 g of low-boiling products were collected in a cold trap downstream of the apparatus. Stirring was continued for 1 hour at 215° C. 180 g of a reaction mixture were obtained, which were reacted with water at 155° C. in a manner corresponding to Example 1. 167 g of crude vinylphosphonic acid were obtained.

EXAMPLE 8

300 g of 2-acetoxyethanephosphonic acid dimethyl ester and 6 g of dimethylformamide were heated with stirring at 215° C. 104 g of methyl acetate were distilled off via a column in the course of 5 hours and 35 minutes. 7.5 g of low-boiling products were collected in a cold trap downstream of the apparatus. 180 g of a reaction mixture were obtained, which were reacted with water at 160° C. in a manner corresponding to Example 1. 167 g of crude vinylphosphonic acid were obtained.

EXAMPLE 9

A mixture of 100 g of vinylphosphonic acid and 150 g of 2-acetoxyethanephosphonic acid dimethyl ester were heated with stirring to 175° C., during which period methyl acetate began to distil off. 3000 g of 2-acetoxyethanephosphonic acid dimethyl ester were then added dropwise in the course of 34 hours at 180° C. while continuing to distil off methyl acetate at the same time, and the resulting reaction mixture was then heated for a further 3 hours at 205° C. The reaction mixture was then reacted with water at 155°–160° C., while the methanol formed was distilled off via a column with a silver-coated jacket. 1760 g of a crude vinylphosphonic acid were obtained, which contained 82% of vinylphosphonic acid, 3.9% of vinylphosphonic acid ester of 2-hydroxyethanephosphonic acid of the structure

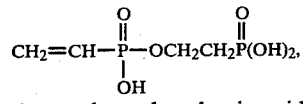

1.3% of 2-hydroxyethanephosphonic acid and 10% of phosphoric acid, relative to the total amount of phosphorus signals in a $^{31}$P-NMr spectrum.

I claim:

1. A process for the preparation of vinylphosphonic acid, which comprises heating a 2-acetoxyethanephosphonic acid dialkyl ester of the general formula

in which R denotes an alkyl group having 1 to 4 carbon atoms, in the presence of acid or basic catalysts at 150° to 270° C. with elimination of an alkyl acetate and thereafter hydrolyzing the remaining reaction mixture with water at temperatures between 150° and 230° C. while simultaneously distilling off the alcohol formed.

2. The process as claimed in claim 1, wherein the elimination of the alkyl acetate is carried out at 170°–230° C. and the hydrolysis is carried out at 140°–175° C.

* * * * *